United States Patent
Swenson

(10) Patent No.: US 6,395,559 B1
(45) Date of Patent: May 28, 2002

(54) MULTIPLE FLUID SAMPLE PROCESSOR WITH SINGLE WELL ADDRESSABILITY

(75) Inventor: Rolf E. Swenson, West Windsor, NJ (US)

(73) Assignee: Orchid BioSciences, Inc., Princeton, NJ (US)

( * ) Notice: Subject to any disclaimer, the term of this patent is extended or adjusted under 35 U.S.C. 154(b) by 0 days.

(21) Appl. No.: 09/304,870

(22) Filed: May 4, 1999

(51) Int. Cl.$^7$ .......................... G01N 33/53; G01N 1/10; B01L 11/00

(52) U.S. Cl. ...................... 436/180; 436/528; 436/531; 436/532; 436/89; 530/333; 530/334; 422/99; 422/100; 422/104; 422/131; 422/134; 435/6; 435/287.2; 435/287.3; 435/288.3; 435/288.4

(58) Field of Search ................. 422/99, 100, 104, 422/131, 134; 435/6, 287.1, 287.2, 287.3, 288.3, 288.4; 436/528, 531, 532, 63, 89, 180; 530/333, 334

(56) References Cited

U.S. PATENT DOCUMENTS

| | | | |
|---|---|---|---|
| 4,517,338 A | * 5/1985 | Urdea et al. ............. 525/54.11 |
| 4,803,050 A | * 2/1989 | Mack ........................... 422/65 |
| 5,143,854 A | * 9/1992 | Pirrung et al. .............. 436/518 |
| 5,324,483 A | * 6/1994 | Cody et al. ................. 422/131 |
| 5,384,261 A | * 1/1995 | Winkler et al. ............. 436/518 |
| 5,429,807 A | * 7/1995 | Matson et al. .............. 422/131 |
| 5,432,091 A | * 7/1995 | Bailey et al. ................. 436/87 |
| 5,449,754 A | * 9/1995 | Nishioka .................... 530/334 |
| 5,476,924 A | 12/1995 | Fraser-Reid et al. |
| 5,585,275 A | * 12/1996 | Hudson et al. .............. 422/129 |
| 5,643,738 A | 7/1997 | Zanzucchi et al. |
| 5,698,522 A | 12/1997 | Haviv et al. |
| 5,700,916 A | 12/1997 | Kahne et al. |
| 5,708,163 A | 1/1998 | Danishefsky et al. |
| 5,744,305 A | 4/1998 | Fodor et al. |
| 5,759,823 A | 6/1998 | Wong et al. |
| 5,763,263 A | * 6/1998 | Dehlinger ................... 435/287 |
| 5,792,431 A | * 8/1998 | Moore et al. ............... 422/134 |
| 5,807,522 A | * 9/1998 | Brown et al. ................. 422/50 |
| 5,807,525 A | * 9/1998 | Allen et al. ................. 422/131 |
| 5,861,492 A | 1/1999 | Kahne |
| 5,874,219 A | 2/1999 | Rava et al. |
| 5,929,208 A | * 7/1999 | Heller et al. ................ 530/333 |
| 6,001,311 A | * 12/1999 | Brennan ..................... 422/131 |
| 6,030,917 A | * 2/2000 | Weinberg et al. ........... 502/104 |
| 6,168,914 B1 | * 1/2001 | Campbell et al. ........... 422/130 |

FOREIGN PATENT DOCUMENTS

WO    WO96/15576    * 5/1996

OTHER PUBLICATIONS

Article: "A Strategy for the Solid–Phase Synthesis of Oligosaccharides," Samuel J. Danishefsky, Science, vol. 260, May 28, 1993.

Article: "Automated Synthesis of Peptides", R. B. Merrifield, Science, vol. 150, Oct. 8, 1965.

Article: "Parallel Synthesis and Screening of a Solid Phase Carbohydrate Library," Rui Liang, Science, vol 274, Nov. 29, 1996.

Article: "The Rubidium Magnetometer in Archeological Exploration," Sheldon Breiner, Science, Oct. 8, 1965.

* cited by examiner

Primary Examiner—Jill Warden
Assistant Examiner—Kathryn Bex
(74) Attorney, Agent, or Firm—Kevin G. Mierzwa

(57) ABSTRACT

A method for single well addressability in a sample processor with row and column feeds. A sample processor or chip has a matrix of reservoirs or wells arranged in columns and rows. Pressure or electrical pumping is utilized to fill the wells with materials. In a preferred embodiment, single well addressability is achieved by deprotecting a single column (row) and coupling each transverse row (column) independently. After the coupling step, the next column (row) is deprotected and then coupling via rows (columns) is performed. Each well can have a unique coupling event. In other embodiments, the chemical events could include, for example, oxidation, reduction or cell lysis.

28 Claims, 4 Drawing Sheets

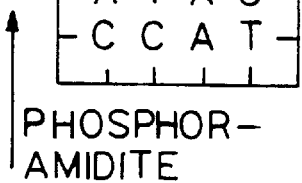
FIG.17A
FIG.17B
FIG.17C
FIG.17D
FIG.17E
FIG.17F

MULTIPLE FLUID SAMPLE PROCESSOR WITH SINGLE WELL ADDRESSABILITY

TECHNICAL FIELD

The present invention relates to fluid sample processors, particularly those used in combinatorial chemistry and DNA synthesis.

BACKGROUND OF THE INVENTION

There are several multiple fluid sample processors known today, particularly those which are micro in size and are able to carry out from dozens to hundreds of experiments and analyses simultaneously. These devices, often called microfluidic devices, have particular use in combinatorial chemistry and DNA synthesis. These devices provide discovery and diagnostic tools which increase the speed and productivity of discovering new drug candidates and analyzing DNA materials, and do so on a miniaturized scale or platform that reduces cost and manual handling.

Many of the known devices utilize a plurality of layers, such as a feed-through layer, a fluidic delivery layer, and a well plate layer. A network of apertures and passageways in the various layers allow passage and transport of various materials and reagents to specific channels and wells for processing. Various mechanisms, such as electro-osmosis or pressure pumping precisely control the flow of materials in the processor.

These devices typically have a network or grid of openings and wells, arranged in rows and columns. Typically, materials added to the processor such as reagents are utilized to fill or couple with an entire row or an entire column of wells and reservoirs. This creates a problem where it is desired to address each well on an individual basis during, for example, DNA synthesis.

With pressure pumping on a microfluidic processor or chip, for example, the reagents are added to all of the wells in a single row or all of the wells in a single column, but it is not possible to individually add reagents separately to each well. There is a need, however, to spatially address each well for applications in oligonucleotide (DNA), peptide, and oligosaccharide synthesis, as well as biological assays. Single well addressability would also be useful in combinatorial libraries for drug discovery or catalyst optimization.

SUMMARY OF THE INVENTION

It is an object of the present invention to provide a new and improved multiple fluid sample processor, system and method, particularly for use in oligomeric synthesis including DNA, peptides, oligosaccharides and other repetitive chemical or biological processes. It is another object of the present invention to provide a system and method for individually addressing wells set up in a column and row format in a multiple fluid sample processor.

It is another object of the invention to provide a liquid handling diagnostic and analysis tool which increases the speed and productivity of synthesis, discovery of new drug candidates, primers or probes for genotyping, and antigen or epitope identification, and to do so on a miniaturized scale or platform that reduces cost and manual handling.

Other objects, purposes, and advantages of the present invention will become apparent in the following description of the invention, particularly when viewed in accordance with the attached drawings and appended claims.

In accordance with the present invention, a multiple fluid sample processor, system, and method are provided which utilizes a multi-layered fluidic array having micro-sized reservoirs, connecting micro channels and reaction cells and wells. Micro-sized wells typically range in sizes from 10 nl to 10 $\mu$l and more particularly from 100 nl to 1 $\mu$l. Micro-sized channels typically range in diameter from 10 microns to 5 millimeters and more particularly from 50 microns to 1 millimeter. A three-dimensional architecture of micro channels and micro-reaction vessels are constructed in the layers in order to transport reagents and other materials throughout the structure.

For a multi-layered device, the array preferably includes a top feed-through plate, a middle distribution plate, and a bottom well plate. The top feed-through plate serves as a cover for the array and contains micro-channels which direct materials to apertures selectively positioned above reservoirs located in the central distribution plate or layer. The apertures are in communication with micron-size reservoirs, micro channels, reservoir feeds, cell feeds, and overflow feeds, which are selectively formed in the center distribution plate. The channels and reservoirs form a delivery system where reservoirs are grouped into elongated columns and rows. In this manner, when a solution or materials is added to one of the apertures in the top plate, it is routed and distributed to fill all of the reservoirs or wells along a column or row in the distribution plate, which could be 6, 8, 10 or more reservoirs or wells. Then the materials in each reservoir or well in that column or row are all treated in the same manner and exposed to the same processing collectively.

Various fluid delivery mechanisms can be utilized to distribute the reactions and other fluids in the display array and to fill the appropriate reservoirs. These mechanisms include pressurized fluid delivery systems, electro-osmosis and electrohydrodynamic distribution.

The present invention provides a system for single well addressability when the chemistry employs, for example, a deprotection followed by a coupling step. Single well addressability is achieved by deprotecting a single column (row) of reaction wells and then coupling each row (column) of wells independently. After the coupling steps, the next column (row) is deprotected and then coupling the rows (columns) is performed. In this manner, each well can have a unique coupling event. Efficiency may be increased, of course, when different wells require the same coupling event. The system can be further optimized by organization of desired compounds to groupings requiring similar reagents.

In accordance with the present invention, when it is necessary or desired to address single reservoirs or wells individually, a particular column or row is deprotected and an appropriate material or reagent is added to a transverse row or column. Another transverse row adds another material to a second individual reservoir. By selectively deprotecting the rows and columns in this manner, each well or reservoir in the fluidic array can be addressed individually, allowing testing and analysis at each one separately.

The present invention can be utilized in any synthesis or analysis in which a chemical event takes place. Typically, these events include deprotection of a protecting group with an acid or base, but they could also include generally any activation event, such as oxidation, reduction or cell lysis followed by hybridization or antibody recognition.

With the present invention, miniaturized liquid handling systems are provided which perform the biological, chemical, and analytical processes fundamental to life sciences, research, and development. Hundreds of reactions can be performed in a microfluidic array device with each of the wells being able to provide a separate and distinct reaction and result. The present invention substantially reduces the time, effort, and expense required while improving the quality and quantity of the test results.

With the present invention, arrays of DNA can be synthesized on demand. The processor can be used for a high volume of sample processing and testing, as well as a search for new molecular targets and determining expression levels and response to known drugs. The processor can incorporate multiple assay formats, such as receptor binding, antibody-antigen interactions, DNA/RNA amplification and detection, as well as magnetic bead base separations. The versatility of the processor makes it available for use with synthesized work stations, genomic support stations, and analytical preparation systems.

BRIEF DESCRIPTION OF THE DRAWINGS

FIGS. 8–16 illustrate a representative system and method for individually addressing single wells of a processor in accordance with the present invention; and FIGS. 17A–F illustrate a representative use of the present invention for a particular DNA synthesis.

Figure 1:
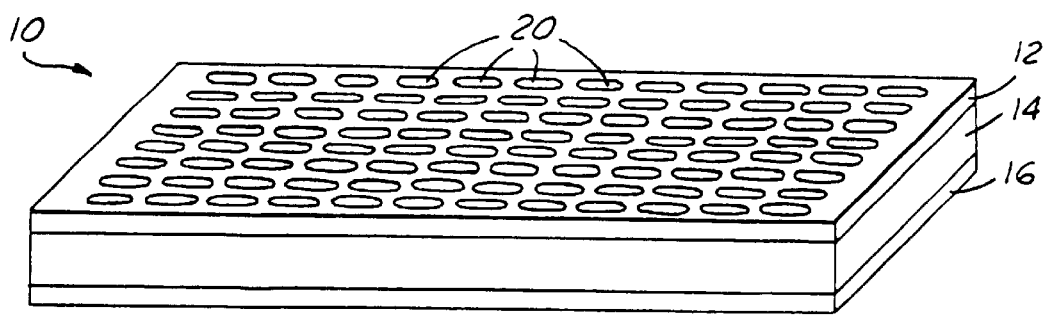
FIG. 1 illustrates a multiple fluid sample processor which can be used with the present invention.

Best MODE(S) FOR CARRYING OUT THE INVENTION

As indicated above, the present can be used in any synthesis or analysis in which a chemical event takes place. These include synthesis of oligonucleotide (DNA) arrays, oligosaccharide arrays, peptide arrays and biological arrays. Typically, synthesis events include deprotection of a protecting group with an acid or base, but they could also include generally any activation event, such as oxidation, reduction or cell lysis followed by hybridization or antibody recognition.

In peptide synthesis, polypeptides may be synthesized by techniques known to those skilled in the art as, for example, by so-called "solid phases" peptide synthesis or by usual methods of solution phase chemistry. A summary of available solid phase peptide synthetic techniques may be found in Stewart et al., *Solid Phase Peptide Synthesis* (W. H. Freeman Co., San Francisco, 1963) and Meienhofer, *Hormonal Proteins and Peptides*, Vol. 2., p. 46 (Academic Press-New York, 1973). For classical solution synthesis see Schroder et al., The Peptides, vol. 1, (Academic Press—New York, 1965).

In general, these methods comprise the sequential addition of one or more amino acids or suitably protected amino acids to a growing peptide chain bound to a suitable resin. The starting amino acids are commercially available or can be synthesized in any conventional manner, where novel in the compounds of this invention, are synthesized by methods detailed below from readily available or can be synthesized in any conventional manner.

Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conducive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by a solid phase method, is cleaved from the solid support to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

In oligonucleotide synthesis, the present invention allows single well addressability during synthesis of oligonucleotides of defined sequences. This synthesis is generally based on the concept of polymeric-support-mediated synthesis strategy in DNA synthesis pioneered by Letsinger and Mahadevan (Letsinger, R L and Mahadevan, V (1995) *Stepwise Synthesis of Oligodeoxyribonucleotides on an Insoluble Polymer Support. J. Am. Chem. Soc.* 87, 3526), similar to the strategy simultaneously developed by R. B. Merrifield (Merrifield, RB (1965) *Automated Synthesis of Peptides. Science* 150, 178) in peptide synthesis. Most oligonucleotide syntheses today are carried out on a solid support, which is prederivatized with a desired nucleoside via a stable covalent linkage. On completion of synthesis, the desired oligonucleotide is released from the support. Generally, oligonucleotide synthesis is performed in 3'–5' direction by the addition of the nucleoside-phosphorus derivative. In chemical terms, the addition of a reactive nucleoside that grows the chain is comprised of several steps. During the chain assembly, these steps are repeated in a cyclic manner. The steps are defined as:

1. Detitylation, i.e., removal of dimethoxytrityl group from the 5' end of nucleoside/nucleotide with dichloroacetic acid solution;
2. Washing, to remove the released dimethoxytrityl cation and excess acid used;
3. Coupling, that is, addition of reactive nucleoside-phosphorus derivative to grow the desired chain with the help of an activator;
4. Washing, to remove excess reagent used for coupling;
5. Oxidation, to convert the labile phosphorus linkage between two nucleoside into a stable phosphate triester or diester;
6. Washing, to remove excess oxidizer from the support; and
7. Capping, to block the unreacted/free hydroxyl group that did not couple to reactive nucleoside-phosphorus derivative during the coupling step.
8. Repeat steps 1–7 until the desired oligonucleotide chain is assembled.

The preparation of oligosaccharides with this invention can be accomplished with a variety of known methods. In standard oligosaccharide chemistry a sugar molecule contains a free hydroxyl group, which can couple with another sugar via an activated leaving group, these two sugars are referred to as the donor and acceptor sugars. Often the sugars may have masked donating or activating groups, which can be chemically modified to reveal their acceptor or donating functional groups. The classical method for completing this coupling of two sugars was the Koenigs-Knorr method where the acceptor has a bromine leaving group and the donor was a hydroxyl group. Recent improvements in sugar chemistry have included the procedures of Danishefsky, Kahne, Fraser-Reid and Wong. (See U.S. Pat. Nos: 5,708,163, 5,700,916, 5,861,492, 5,476,924, and 5,759,823.) In each of these methods, the chemical activating procedure is either dimethyldioxirane oxidation (Danishefsky), MCPBA oxidation (Kahne), Bromine addition (Freiser-Reid) or attachment of appropriate functional group for enzymatic coupling. The methods of Danishefski and Kahne have been shown to also work on solid supports.

In the most basic application of this discovery, a sugar, attached to a solid support, is in each of the wells of the chip. Each column is sequentially chemically activated and a donor sugar introduced via rows. Different sugars could be added via each row as in the scheme below. Other protecting groups on the sugars can be removed before or after cleavage from the solid support. Types of solid support and methods of cleavage can be found in either Danishefsky et al, *A Strategy for the Solid-Phase Synthesis of Oligosaccharides*, Science, Vol. 260, p. 1307–1309 (1993), or Liang et al, *Parallel Synthesis and Screening of a Solid-Phase Carbohydrate Library*, Science, Vol. 274, p. 1520–2 (1996).

An efficient way for generating a large number of individual compounds is to use the methods of combinatorial chemistry in which the compounds are mixed and split into individual wells. In this regard, the present invention can be used for either solid-phase or solution-phase combinatorial chemistry. For ease of describing the present invention, it will be described for use in solid-phase processing. It will be obvious to persons of ordinary skill in the art, however, that such use is not limiting and that the present invention can be used in a similar and equivalent manner for solution-phase processing as well.

For solid-phase chemistry, a core compound is attached to a solid support and divided into a "N" number of pools. Each pool has the functional group derivatized on the core with additional functionality (such as monomer, diversiomer, etc.). This produces cores A1–AN. The derivatized cores are then mixed and split into an "M" number of pools and derivatized in the same manner. After two derivatizations, N×M compounds are produced from the N+M different reactions. This method has been automated, but is frequently a manual process. Compound tracking on the solid support can be done by tagging each chemical step either by a chemical method or a radiofrequency tag.

Another efficient manner to obtain combinatorially generated compounds is the implementation of individual wells that can be addressed by reagents from rows or columns. With this system, an "R" number of compounds in "N" columns and "M" rows would generate similar M×N=R compounds from M+N reagents. This is accomplished by microfluidic delivered reagents to wells in a silicone or glass chip. These chips typically have row, column, and matrix feeds, and combinatorial chemistry can be performed in them.

A limitation of row-column combinatorial chemistry is that each compound in the same row or column and the same RN or RM group is attached to it. Single well addressability is not possible. This disadvantage is particularly significant where multi-step synthesis is employed to make oligomeric molecules such as oligonucleotides, oligosaccharides, or peptides, where each product may have similar character, but a unique structural form. This limitation also impacts the overall diversity of libraries prepared for drug discovery or catalyst screening.

The present invention provides a solution to row/column combinatorial libraries, and generates single well addressability without individual control of each well. In particular, in accordance with one embodiment, the present invention uses orthogonal protecting groups as well as the matrix architecture row/column delivery of reagents.

A typical processor which can be used in accordance with the present invention generally incorporates a modular configuration with distinct layers or plates. The processor is capable of conducting parallel synthesis of dozens, hundreds, or even thousands of small molecular compounds through the precise delivery of reagents to discreet reaction sites. This helps create a significantly larger number and variety of small molecules more effectively and with fewer resources. With the present invention, arrays of DNA can be synthesized on demand. The processor can also be used for high volume of sample processing and testing, as well as a search for new molecular targets and determining expression levels and responses to known drugs. The processor can incorporate multiple assay format, such as receptor binding, antibody-antigen interactions, DNA/RNA amplification and detection, as well as magnetic bead base separations. The processor is versatile and is available for use with synthetic work stations, genomic support stations, and analytical preparation systems.

Figure 2:
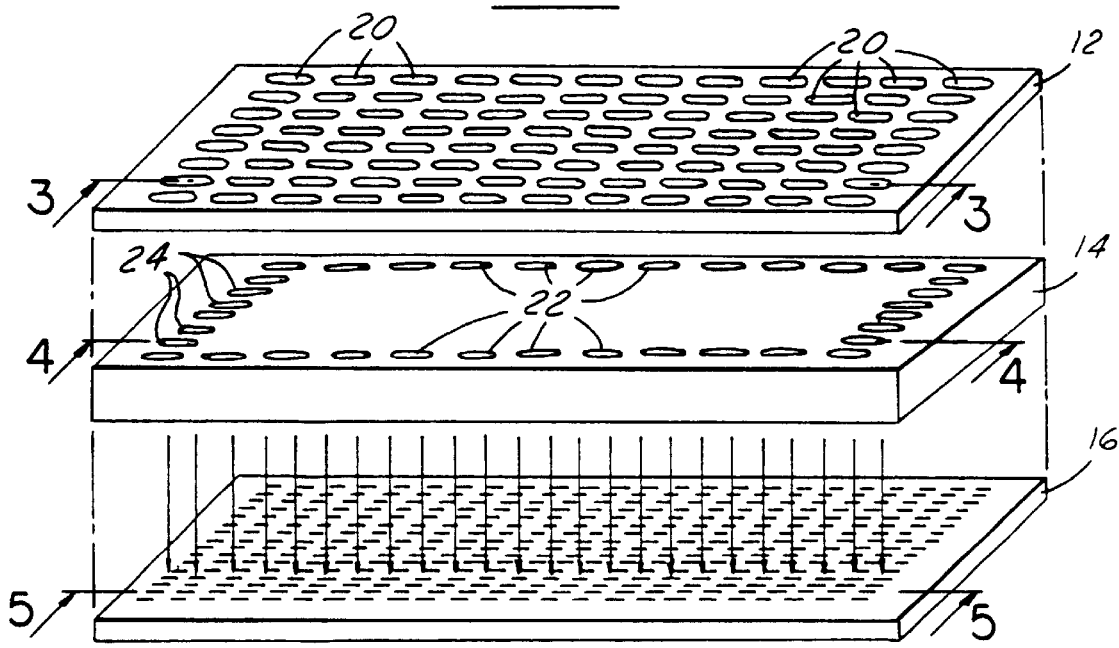
FIG. 2 is an exploded view of the sample processor shown in FIG. 1.
Figure 3:
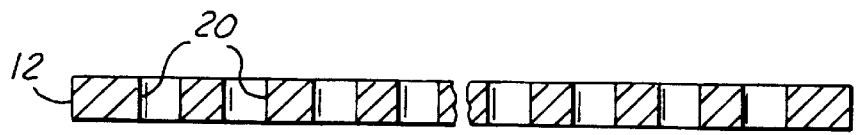
FIG. 3 is a cross-sectional view of the top layer of the processor shown in FIGS. 1 and 2, the cross-section being taken along line 3—3 in FIG. 2.
Figure 4:
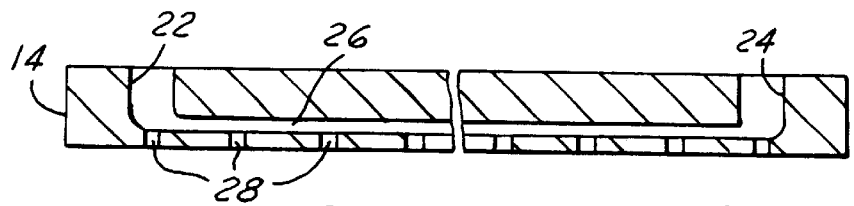
FIG. 4 is a cross-sectional view of the middle layer of the processor shown in FIGS. 1 and 2, the cross-section being taken along line 4—4 in FIG. 2.
Figure 5:
FIG. 5 is a cross-sectional view of the bottom or well plate layer of the processor shown in FIGS. 1 and 2, the cross-section being taken along line 5—5 in FIG. 2.

A representative multiple fluid sample processor for use in the present invention is shown in FIGS. 1 and 2, with cross-sections of the layers being shown in FIGS. 3, 4, and 5. The processor, which is generally referred to by the reference number 10, is a three layer structure in the embodiment illustrated. It is also understood that the processor can include a larger or smaller number of layers, as needed or desired for the particular chemical or DNA operations desired to be performed.

Processor 10 includes a top layer 12, which is also called a reagent reservoir. The processor also includes a middle layer 14, also called a fluidic delivery or distribution layer. The bottom layer 16 is also called a well chip, and includes a plurality of individual wells or containers.

The top layer feeds compounds and materials into the processor 10 and also serves as a cover for it. The layer 12 contains a number of apertures 20, which are selectively positioned immediately above openings 22, 24 in the reservoir or fluidic delivery layer 14. The openings 22, 24 are connected by an elongated micro-channel 26 which, in turn, has a plurality of small passage channels 28.

The bottom or lower plate member 16 has a plurality of reservoirs or wells 30 which are used to hold the reagents and other materials in order for them to react and synthesize. Each of the reaction wells 30 has an entrance channel 32 and an exhaust or drain channel 34.

The three layers 12, 14, and 16, are stacked together to form a modular configuration. They also are typically coupled together tightly to form a liquid-tight seal. Sealing gaskets or members can be utilized, if necessary. If desired, the top layer 12 can be bounded or fused to the central distribution plate 14. The bottom or well plate is typically detachably coupled to layer 14 or a combination of layers so they can be removed for further processing and/or testing of the materials in the wells 30.

The plates 12, 14, and 16 can be made from any desirable material, such as glass, fused silica, quartz, or silicon wafer material. The reservoirs, micro-channels and reaction cells are controllably etched or otherwise formed into the plates using traditional semiconductor fabrication techniques with a suitable chemical or laser etchant.

In order to provide a small, cost efficient analytical device, the channels, wells and reaction cells are preferably provided on a micro-sized level. In this regard, the micro-sized wells typically range in size from 10 nl to 10 $\mu$l; and more particularly from 100 nl to 1 $\mu$l. The cross-sectional dimensions of the micro-channels typically range in size from 10 microns to 5 millimeters, and more particular from 50 microns to 1 millimeter.

A pressure pumping mechanism (not shown) can be used to assist in loading and distributing the reagents and other materials within the layers. After the reagents or other materials are passed through apertures 20 in the top layer 12, the pressure mechanism applies air pressure sufficiently in order to distribute the materials evenly along channel 26 and into each of the reaction reservoirs or wells 30. The pressure exerted by the pressure mechanism conveys the liquids through the small passageways 28 and 32 until the materials reside in the larger reaction wells.

Subsequently, when it is desired to empty or exhaust the materials from the reaction wells, pressure is increased in the pressure mechanism sufficiently to exhaust materials from the reaction wells. For this purpose, a collection or drain plate (not shown) can be positioned immediately below the processor 10 during its use.

The particular well chip 16 shown in FIGS. 1 and 2 is a 384-well sample plate. Standard well plates are typically provided in multiples of 96, with a 96-well sample plate being commonly used. Larger multiples of 96 can also be utilized. The detachable layers are preferably of a common dimensionality for ease of handling by robotic or other automation means. A common set of dimensions has been adopted by many manufacturers which match that of a 96-well plate known as a "microtiter" plate. Due to the column and row format of the processor 10, a material entering apertures 22 or 24 and being transferred along channel 26 is introduced into every well 30 along that column or row.

In order to perform a separate or individual reaction or synthesis on a material in one particular specific well, the present invention is utilized. A simple example of the present invention is provided below. Although the sample illustrates the use of the invention with a three column—three row processor or sequence, it is to be understood that the same rationale and principles can be applied to processors having greater numbers of rows and columns. Also, although the sample illustrates the use of the invention for DNA (oligonucleotide) synthesis, it is to be understood that the invention can be used for numerous other chemical events, such as peptide synthesis, oligosaccharide synthesis, and biological assays. For example, for biological assays, the deprotection step is cell lysis and the coupling step is hybridization.

For a matrix structure of wells, the number of wells is represented by the formula N×M, where N represents the number of rows and M represents the number of columns. A simple chemical sequence can be defined as protection and coupling. For this purpose, it is assumed that deprotection and coupling are orthogonal events. In this regard, a core must be deprotected prior to coupling and, if it has not been deprotected or has not already been coupled to another material, then no additional coupling is possible. In accordance with the present invention, single well addressability can be obtained if the deprotection step is done one column or row at a time and the coupling is performed in each column or row independently, either sequentially or in parallel.

Figure 6:
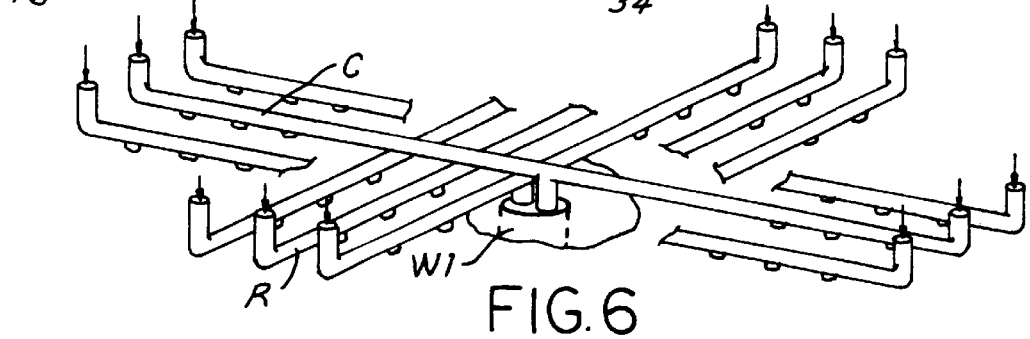
FIG. 6 is a schematic diagram of the processor showing column and row addressability thereof.
Figure 7:
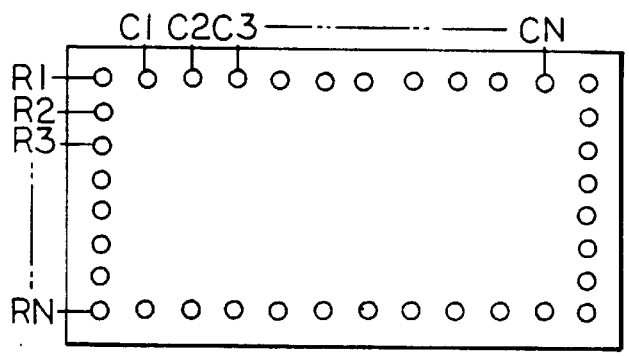
FIG. 7 is a top view of the processor network showing the columns and rows.
Figure 8:
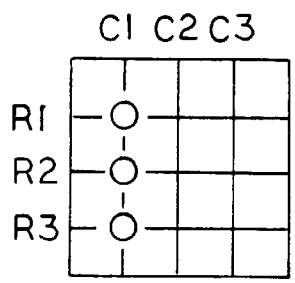
Figure 9:
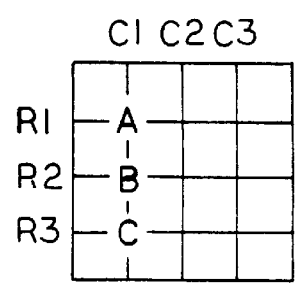

FIGS. 6 and 7 show schematically a representative matrix in a processor showing the columns and rows. As shown, each column C and row R has an entrance into a single well W1. The intersections of each of the rows and columns represents a single well. Thus, each well can be served either by a column or row operation.

FIGS. 8–16 illustrate the representative use of the invention with a 3×3 matrix structure, that is where M=3 and N=3. Each well is provided with a core on, for example, a solid support. Thus, the first step of the sequence is adding the core to the solid support, in a typical fashion. Thereafter, the first or next step of the method in accordance with the present invention is to deprotect all of the materials in a certain row or column. In this example, column C1 is deprotected. This is typically done by use of an acid for DNA synthesis, such as $CCl_3CO_2H$. (For peptide synthesis with Fmoc protection, a base, such as piperdine, or with t-Boc protection, an acid such as trifluoracetic acid can be utilized; for oligosaccharide synthesis, MCPBA or dimethyldioxirane can be utilized; and for biological assays, a lysis buffer can be utilized.) A circle on an intersection indicates that the material in that well is deprotected and thus is open to reaction with another material or reagent.

In the next step of the process, material A is added to row R1, material B is added to row R2, and material C is added to row R3. This is shown schematically in FIG. 9. Since only the intersections of C1-R1, C1-R2, and C1-R3 are deprotected, the materials A, B, and C are only present in the particular wells shown.

Figures 10, 11, 12, 13, 14, 15, 16:
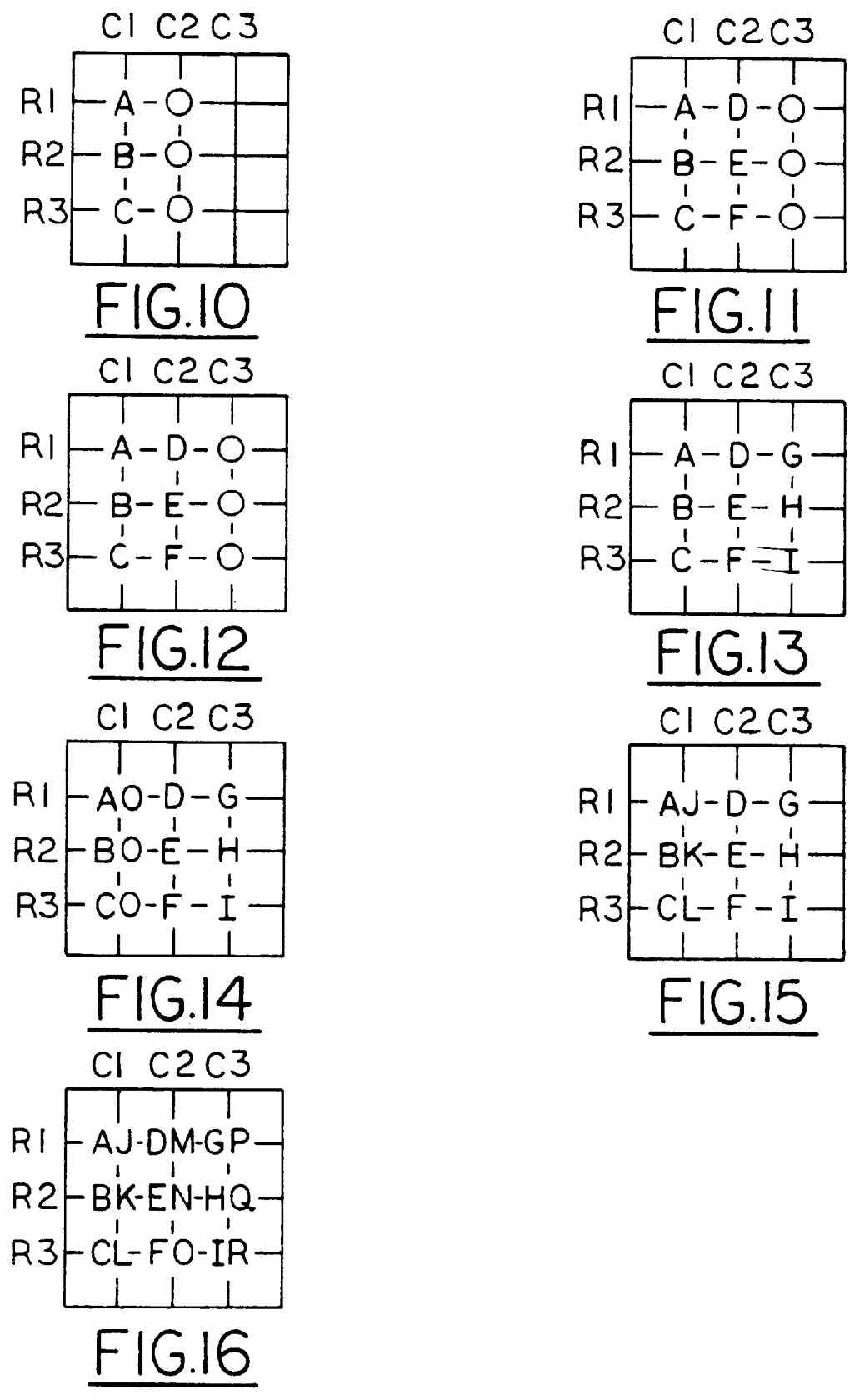

In the next step of the process, column C2 is deprotected. This is shown in FIG. 10. Thereafter, material D is added in row R1, material E is added in row R2, and material F is added in row R3, as shown in FIG. 11. Thereafter, column C3 is deprotected, as shown in FIG. 12, and materials G, H, and I are added to rows R1, R2, and R3, respectively, as shown in FIG. 13.

At this point, the wells contain materials A, B, and C along column C1 are again deprotected. This is shown in FIG. 14. Materials J, K, and L are then added in rows R1, R2, and R3 respectively. This forms compounds AJ in well C1-R1, compound BK in well R2-C1, and material CL in well R3-C1, as shown in FIG. 15.

Two other cycles of deprotection and the adding of additional coupling agents produce nine separate dual functionalized cores, as shown in FIG. 16. Even though the coupling agent is added to all the wells in a particular row, the protecting scheme insures that only one compound is coupled per row. The present example is a scenario in which there is little commonality of coupling reagents being employed and is analogous to amino acid coupling without describing wash cycles. It is clear that where several of the wells have the same material and are subject to the same processing steps, that a fewer number than nine separate cores can be formed and utilized.

Another example for use in the present invention is where during each cycle of deprotection/coupling, it is decided to use either row or column for deprotection and the corresponding column or row for coupling. This takes advantage of similarity in reagents being coupled and is often encountered in DNA synthesis.

In this regard, the present invention can be used to synthesize 16 unique DNA 6 mers. The six matrixes or boxes shown in FIGS. 17A to 17F show each of the bases added to each step organized to emphasize homology. In this example, the sixteen DNA 6 mers are as follows:

1. AGAATA
2. GATGTC
3. CGCTTA
4. GACCTT
5. CAATTG
6. TGTGTG
7. CCGATC
8. TATATA
9. ACGCCT
10. TATGGT
11. AGTCGT
12. GCACAT
13. CTGGAT
14. CCCGCT
15. ATCCGT
16. TGATCT

While particular embodiments of the invention have been shown and described, numerous variations and alternate embodiments will occur to those skilled in the art. Accordingly, it is intended that the invention be limited only in terms of the appended claims.

What is claimed is:

1. A method for addressing wells individually in a fluid processing device having a plurality of N column channels and a plurality of M row channels and a plurality of wells arranged in a matrix of N columns and M rows, each of said row channels and column channels having a respective opening corresponding to said plurality of wells, said method comprising:
   deprotecting a first of N columns of wells with a first deprotecting agent through a first of said plurality of column channels while protecting each of said N columns except the first of N columns;
   coupling M rows of wells with a respective first plurality of coupling agents through said plurality of row channels;
   deprotecting a second of N columns of wells with a second deprotecting agent through a second of said plurality of column channels while protecting each of said N columns except the second of N columns of wells;
   coupling M rows of wells with a respective second plurality of coupling agents through said plurality of row channels; and
   continuing the deprotecting and coupling steps until all N columns of wells and M rows have been addressed.

2. The method for addressing wells as recited in claim 1 wherein said first deprotecting agent and said second deprotecting agent are the same.

3. The method for addressing wells as recited in claim 1 said first plurality of coupling agents and said second plurality of coupling agents are the same.

4. The method for addressing wells as recited in claim 1 wherein said columns and rows of wells of said fluid processing device are filled by pressure pumping.

5. The method for addressing wells as set forth in claim 1 wherein the fluid processing device is being used for peptide synthesis.

6. The method for addressing wells as set forth in claim 1 wherein said first plurality and second plurality of coupling agents are selected from the group comprising N-protected amino acids, diisopropyl carbodiinide, and peptide coupling agents.

7. A method for addressing wells individually in a fluid processing device having a plurality of N column channels and a plurality of M row channels and a plurality of wells arranged in a matrix of N columns and M rows, each of said row channels and column channels having a respective opening corresponding to said plurality of wells, said method comprising the steps of:
   adding a first cell lysis buffer to a first of N columns of wells through said plurality of column channels while protecting each of said N columns except the first of N columns;
   adding a solution containing a fluorescently labeled DNA to M rows of wells through said plurality of row channels;
   adding a second cell lysis buffer to a second of N columns of wells through a second of said plurality of column channels while protecting each of said N columns except the second of N columns of wells;
   adding a solution containing a fluorescently labeled DNA to M rows of wells through said plurality of row channels; and
   continuing the cell lysis buffer step and DNA solution steps until all N columns of wells and M rows have been addressed.

8. The method for addressing wells as recited in claim 7 wherein said first and second cell lysis buffers are the same.

9. The method for addressing wells as recited in claim 7 wherein all of said solutions containing fluorescently labeled DNA are the same.

10. The method for addressing wells as recited in claim 7 wherein said columns and rows of wells of said fluid processing device are filled by pressure pumping.

11. A method for addressing wells individually in a fluid processing device having a plurality of N column channels and a plurality of M row channels and a plurality of wells arranged in a matrix of N columns and M rows, each of said row channels and column channels having a respective opening corresponding to said plurality of wells, said method comprising the steps of:
   adding a first cell lysis buffer to a first of N columns of wells through said plurality of column channels while protecting each of said N columns except the first of N columns;
   adding a solution containing a fluorescently labeled antibody to M rows of wells through said plurality of row channels;
   adding a second cell lysis buffer to a second of N columns of wells through a second of said plurality of column channels while protecting each of said N columns except the second of N columns of wells;
   adding a solution containing a fluorescently labeled antibody to M rows of wells through said plurality of row channels; and
   continuing the cell lysis buffer step and antibody solution steps until all N columns of wells and M rows have been addressed.

12. The method for addressing wells as recited in claim 11 wherein said first and second cell lysis buffers are the same.

13. The method for addressing wells as recited in claim 11 wherein all of said solutions containing fluorescently labeled antibody are the same.

14. The method for addressing wells as recited in claim 11 wherein said columns and rows of wells of said fluid processing device are filled by pressure pumping.

15. A method for addressing wells individually in a fluid processing device having a plurality of N column channels and a plurality of M row channels and a plurality of wells arranged in a matrix of N columns and M rows, each of said row channels and column channels having a respective opening corresponding to said plurality of wells, said method comprising the steps of:

- oxidizing a first of N columns of wells with a first oxidizing agent through said plurality of column channels while protecting each of said N columns except the first of N columns;
- coupling M rows of wells with a respective first plurality of coupling agents through said plurality of row channels;
- oxidizing a second of N columns of wells with a second oxidizing agent through a second of said plurality of column channels while protecting each of said N columns except the second of N columns of wells;
- coupling M rows of wells with a respective second plurality of coupling agents through said plurality of row channels; and
- continuing the oxidizing and coupling steps until all N columns of wells and M rows have been addressed.

16. The method for addressing wells as recited in claim 15 wherein said first oxidizing agent and said second oxidizing agent are the same.

17. The method for addressing wells as recited in claim 15 wherein said first coupling agent and said second coupling agent are the same.

18. The method for addressing wells as recited in claim 15 wherein said columns and rows of wells of said fluid processing device are filled by pressure pumping.

19. The method as set forth in claim 15 wherein the fluid process device is used for oligosaccharide synthesis.

20. The method as set forth in claim 15 wherein said first and second coupling agents are selected from the group comprising sugar and protected sugar with at least one free hydroxyl group.

21. A method for addressing wells individually in a fluid processing device having a plurality of N column channels and a plurality of M row channels and a plurality of wells arranged in a matrix of N columns and M rows, each of said row channels and column channels having a respective opening corresponding to said plurality of wells, said method comprising:

- reducing a first of N columns of wells with a first reducing agent through a first of said plurality of column channels while protecting each of said N columns except the first of N columns;
- coupling M rows of wells with a respective first plurality of coupling agents through said plurality of row channels;
- reducing a second of N columns of wells with a second reducing agent through a second of said plurality of column channels while protecting each of said N columns except the second of N columns of wells;
- coupling M rows of wells with a respective second plurality of coupling agents through said plurality of row channels; and
- continuing the deprotecting and coupling steps until all N columns of wells and M rows have been addressed.

22. The method for addressing wells as recited in claim 21 said first reducing agent and said second reducing agent are the same.

23. The method for addressing wells as recited in claim 21 wherein said first coupling agent and said second coupling agent are the same.

24. The method for addressing wells as recited in claim 21 wherein said columns and rows of wells of said fluid processing device are filled by pressure pumping.

25. A method for addressing wells individually in a fluid processing device having a plurality of N column channels and a plurality of M row channels and a plurality of wells arranged in a matrix of N columns and M rows, each of said row channels and column channels having a respective opening corresponding to said plurality of wells, said method comprising:

- adding a first reagent to a first of N columns of wells through a first of said plurality of column channels, said reagent activating the material in said wells towards coupling with a subsequently added reagent while protecting each of said N columns except the first of N columns;
- adding a respective second plurality of reagents to M rows of wells through said plurality of row channels, said second reagent coupling with said activate material;
- adding a third reagent to a second of N columns of wells through a second of said plurality of column channels, said third reagent activating the material in said wells towards coupling with a subsequently added reagent, while protecting each of said N columns except the second of N columns of wells;
- adding a respective fourth plurality of reagents to M rows of wells through said plurality of row channels, said fourth plurality of reagents coupling with said activate material;
- continuing the reagent steps until all N columns of wells and M rows have been addressed.

26. The method for addressing wells as recited in claim 25 wherein at least said first and third reagents are the same.

27. The method for addressing wells as recited in claim 25 wherein at least said second plurality and fourth plurality of reagents are the same.

28. The method for addressing wells as recited in claim 25 wherein said columns and rows of wells of said fluid processing device are filled by pressure pumping.

* * * * *